United States Patent
Shekhar et al.

(10) Patent No.: US 12,221,841 B2
(45) Date of Patent: Feb. 11, 2025

(54) VELOCITY MEASUREMENT OF DRILLED CUTTINGS ON A SHAKER

(71) Applicant: Halliburton Energy Services, Inc., Houston, TX (US)

(72) Inventors: Prashant Shekhar, Houston, TX (US); Gillies Alexander MacDonald, Shenandoah, TX (US); Abhijit Kulkarni, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 330 days.

(21) Appl. No.: 17/748,540

(22) Filed: May 19, 2022

(65) Prior Publication Data

US 2022/0275694 A1 Sep. 1, 2022

Related U.S. Application Data

(62) Division of application No. 16/415,908, filed on May 17, 2019, now Pat. No. 11,339,618.

(Continued)

(51) Int. Cl.
*E21B 21/06* (2006.01)
*B01D 33/03* (2006.01)
(Continued)

(52) U.S. Cl.
CPC ........ *E21B 21/065* (2013.01); *B01D 33/0346* (2013.01); *B01D 33/80* (2013.01);
(Continued)

(58) Field of Classification Search
CPC ... E21B 21/065; B01D 33/0346; B01D 33/80; G01B 21/22; G01F 1/663; G01S 13/581
See application file for complete search history.

(56) References Cited

U.S. PATENT DOCUMENTS

| | | |
|---|---|---|
| 4,736,297 A | 4/1988 | Lejeune |
| 4,739,655 A | 4/1988 | Greer et al. |

(Continued)

FOREIGN PATENT DOCUMENTS

| | | |
|---|---|---|
| AU | 2011383364 B2 | 6/2014 |
| CN | 101386235 A | 3/2009 |

(Continued)

OTHER PUBLICATIONS

"U.S. Appl. No. 14/363,264, Advisory Action mailed Apr. 29, 2016", 3 pgs.

(Continued)

*Primary Examiner* — Peter M Bythrow
*Assistant Examiner* — Nazra Nur Waheed
(74) *Attorney, Agent, or Firm* — DeLizio, Peacock, Lewin & Guerra LLP

(57) ABSTRACT

An apparatus includes a shaker screen onto which downhole materials and fluid from a borehole are to be placed, the downhole materials a product of a downhole operation and a shaker to vibrate the shaker screen to separate the downhole materials from the fluid. The apparatus includes a radar to emit an electromagnetic wave onto the downhole materials on at least one of the shaker screen and a transit and detect a reflection of the electromagnetic wave reflected off at least a portion of the downhole materials and a device to determine a velocity of the downhole materials advancing along at least one of the shaker screen toward a discharge end of the shaker screen and the transit.

7 Claims, 7 Drawing Sheets

Related U.S. Application Data

(60) Provisional application No. 62/680,438, filed on Jun. 4, 2018.

(51) Int. Cl.

| | | |
|---|---|---|
| *B01D 33/80* | (2006.01) | |
| *G01B 21/22* | (2006.01) | |
| *G01F 1/663* | (2022.01) | |
| *G01S 13/58* | (2006.01) | |

(52) U.S. Cl.
CPC .............. *G01B 21/22* (2013.01); *G01F 1/663* (2013.01); *G01S 13/581* (2013.01)

(56) References Cited

U.S. PATENT DOCUMENTS

| | | | |
|---|---|---|---|
| 5,663,559 | A | 9/1997 | Auzerais et al. |
| 5,947,213 | A | 9/1999 | Angle et al. |
| 6,378,627 | B1 | 4/2002 | Tubel et al. |
| 6,386,297 | B1 | 5/2002 | Cooley et al. |
| 7,139,219 | B2 | 11/2006 | Kolléet al. |
| 7,272,504 | B2 | 9/2007 | Akimov et al. |
| 7,299,136 | B2 | 11/2007 | Difoggio et al. |
| 7,446,885 | B2 | 11/2008 | Zabolitzky et al. |
| 7,634,059 | B2 | 12/2009 | Wraight |
| 7,705,294 | B2 | 4/2010 | Ramstad et al. |
| 7,835,568 | B2 | 11/2010 | Park et al. |
| 8,483,445 | B2 | 7/2013 | Tjhang et al. |
| 8,550,158 | B1 | 10/2013 | Shaposhnikov |
| 8,567,526 | B2 | 10/2013 | Johnston et al. |
| 9,228,401 | B2 | 1/2016 | Edwards et al. |
| 9,576,374 | B2 | 2/2017 | Elkington et al. |
| 10,174,578 | B2 | 1/2019 | Walton et al. |
| 10,509,141 | B2 | 12/2019 | Maeso et al. |
| 10,605,077 | B2 | 3/2020 | Aird |
| 10,634,807 | B2 | 4/2020 | Tang et al. |
| 2005/0216197 | A1 | 9/2005 | Zamora et al. |
| 2007/0165225 | A1 | 7/2007 | Trainer |
| 2007/0189119 | A1 | 8/2007 | Klotz et al. |
| 2008/0056604 | A1 | 3/2008 | Choe et al. |
| 2008/0192987 | A1 | 8/2008 | Helgason et al. |
| 2009/0020333 | A1 | 1/2009 | Marsh |
| 2009/0087911 | A1 | 4/2009 | Ramos et al. |
| 2009/0259446 | A1 | 10/2009 | Zhang et al. |
| 2010/0135536 | A1 | 6/2010 | Dvorkin et al. |
| 2011/0272144 | A1 | 11/2011 | Belcher et al. |
| 2012/0076364 | A1 | 3/2012 | Tjhang et al. |
| 2014/0020954 | A1 | 1/2014 | Pelletier et al. |
| 2014/0046628 | A1 | 2/2014 | Ligneul et al. |
| 2014/0254884 | A1 | 9/2014 | Elkington et al. |
| 2014/0333754 | A1 | 11/2014 | Graves et al. |
| 2015/0330215 | A1 | 11/2015 | Jamison et al. |
| 2016/0146653 | A1* | 5/2016 | Skelding ................ E21B 21/01 73/861.01 |
| 2016/0298996 | A1* | 10/2016 | Koeroghlian ........... G01F 1/663 |
| 2016/0370274 | A1 | 12/2016 | Rowe et al. |
| 2017/0010387 | A1* | 1/2017 | Huang .................... G01V 11/00 |
| 2017/0058620 | A1 | 3/2017 | Torrione |
| 2017/0089153 | A1* | 3/2017 | Teodorescu ............. E21B 43/10 |
| 2017/0153355 | A1 | 6/2017 | Little, III et al. |
| 2018/0038179 | A1* | 2/2018 | Canty ..................... G06T 7/248 |
| 2019/0368287 | A1 | 12/2019 | Shekhar et al. |
| 2019/0368347 | A1 | 12/2019 | Kulkarni et al. |
| 2020/0332654 | A1 | 10/2020 | Rowe et al. |

FOREIGN PATENT DOCUMENTS

| | | |
|---|---|---|
| GB | 2583860 | 5/2022 |
| WO | 8202573 A1 | 8/1982 |
| WO | 2009069004 A2 | 6/2009 |
| WO | 2013089683 A1 | 6/2013 |
| WO | 2013105930 A1 | 7/2013 |
| WO | 2015002653 A1 | 1/2015 |
| WO | 2015156893 A1 | 10/2015 |
| WO | 2016171650 A1 | 10/2016 |

OTHER PUBLICATIONS

"U.S. Appl. No. 14/363,264, Final Office Action mailed Feb. 10, 2016", 11 pgs.

"U.S. Appl. No. 14/363,264, Non Final Office Action mailed Aug. 12, 2015", 10 pgs.

"U.S. Appl. No. 14/363,264, Preliminary Amendment filed Jun. 5, 2014", 3 pgs.

"U.S. Appl. No. 14/363,264, Response filed Apr. 5, 2016 to Final Office Action mailed Feb. 10, 2016", 10 pgs.

"U.S. Appl. No. 14/363,264, Response filed Nov. 6, 2015 to Non Final Office Action mailed Aug. 12, 2015", 8 pgs.

"Australian Application Serial No. 2011383364, First Examiners Report mailed Dec. 11, 2014", 3 pgs.

"Australian Application Serial No. 2011383364, Response filed Jan. 20, 2015 to First Examiners Report mailed Dec. 11, 2014", 3 pgs.

"Canadian Application Serial No. 2,857,484, Office Action mailed May 12, 2017", 5 pages.

"Canadian Application Serial No. 2,857,484, Office Action mailed Jun. 2, 2016", 4 pgs.

"Canadian Application Serial No. 2,857,484, Office Action mailed Aug. 25, 2015", 3 pgs.

"Canadian Application Serial No. 2,857,484, Response filed Jan. 26, 2016 to Office Action mailed Aug. 25, 2015", 10 pgs.

"Chinese Application Serial No. 201180075476. Office Action mailed Oct. 24, 2017", 11 pages.

"Chinese Application Serial No. 201180075476.6, Office Action mailed Sep. 20, 2016", 26 pgs.

"European Application Serial No. 11877269.8, Extended European Search Report mailed Jul. 28, 2015", 13 pgs.

"European Application Serial No. 11877269.8, Office Action mailed Jul. 15, 2014", 3 pgs.

"European Application Serial No. 11877269.8, Response filed Feb. 17, 2016 to Extended European Search Report mailed Jul. 28, 2015", 11 pgs.

"European Application Serial No. 11877269.8, Response filed Aug. 19, 2014 to Office Action mailed Jul. 15, 2014", 7 pgs.

"Gulf Cooperation Council Application Serial No. 2012/23017, Office Action mailed Jan. 18, 2016", 4 pgs.

"Gulf Cooperation Council Application Serial No. 2012/23017, Office Action mailed Jun. 21, 2016", 4 pgs.

"Gulf Cooperation Council Application Serial No. 2012/23017, Response filed Apr. 4, 2016 to Office Action mailed Jan. 18, 2016", 6 pages.

"Gulf Cooperation Council Application Serial No. 2012/23017, Response filed Oct. 4, 2016 to Office Action mailed Jun. 23, 2016".

"International Application Serial No. PCT/US/2011/064644, Search Report mailed Mar. 29, 2012", 2 pgs.

"International Application Serial No. PCT/US2011/064644, International Preliminary Report on Patentability mailed Feb. 20, 2014", 8 pgs.

"International Application Serial No. PCT/US2011/064644, Response filed May 15, 2012 to Written Opinion mailed Mar. 29, 2012", 3 pgs.

"International Application Serial No. PCT/US2011/064644, Written Opinion mailed Mar. 29, 2012", 6 pgs.

"Malaysian Application Serial No. PI 2014701575, Substantive Examination Adverse Report, mailed Nov. 15, 2017, 3 pgs.", 3 pages.

"Malaysian Application Serial No. PI2014701575, Preliminary Examination—Clear Formalities Report, mailed Sep. 3, 2014", 3 pgs.

U.S. Appl. No. 16/428,458, Non-Final Office Action, mailed Oct. 9, 2020, 12 pages.

U.S. Appl. No. 16/428,458, Final Office Action, mailed Feb. 5, 2021, 13 pages.

U.S. Appl. No. 16/959,014 Non-Final Office Action, mailed Nov. 3, 2021, 13 pages.

U.S. Appl. No. 16/428,458; Non Final Office Action; Aug. 23, 2021, 13 pages.

U.S. Appl. No. 16/959,014; Non Final Office Action; Apr. 26, 2021, 14 pages.

PCT Application Serial No. PCT/US2019/016548, International Search Report, mailed May 20, 2019, 3 pages.

PCT Application Serial No. PCT/US2019/032967, International

(56) References Cited

OTHER PUBLICATIONS

Search Report, mailed Aug. 23, 2019, 3 pages.
PCT Application Serial No. PCT/US2019/035002, International Search Report, mailed Sep. 19, 2019, 3 pages.
GCC Application Serial No. 37513; First Office Action; Jun. 30, 2020, 5 pages.
GCC Application Serial No. 2019-37454; First Office Action; Apr. 28, 2020, 5 pages.
PCT Application Serial No. PCT/US2019/035002, International Written Opinion, mailed Sep. 19, 2019, 5 pages.
PCT Application Serial No. PCT/US2019/016548, International Written Opinion, mailed May 20, 2019, 7 pages.
PCT Application Serial No. PCT/US2019/032967, International Written Opinion, mailed Aug. 23, 2019, 7 pages.
U.S. Appl. No. 16/415,908, Notice of Allowance, mailed Jan. 25, 2022, 8 pages.
Guilherme, et al., "Petroleum well drilling monitoring through cutting image analysis and artificial intelligence techniques", Engineering Applications of Artificial Intelligence, Pineridge Press, Swansea, GB, vol. 24, No. 1, Feb. 1, 2011 (Feb. 1, 2011), pp. 201-207, XP027534455, ISSN: 0952-1976 [retrieved on Nov. 29, 2010], Feb. 1, 2011 00:00:00.0, 6.

\* cited by examiner

VELOCITY MEASUREMENT OF DRILLED CUTTINGS ON A SHAKER

TECHNICAL FIELD

The disclosure generally relates to the field of downhole hydrocarbon recovery, and more particularly to velocity measurement of drilled cuttings on a shaker.

BACKGROUND

Increasing the effectiveness of pumping, sweeping, drilling operations, fracturing operations, etc. can reduce the cost of hydrocarbon recovery operations. An approach to increasing the effectiveness of such operations is to observe the characteristic features of various particles returning to the Earth's surface from downhole during different hydrocarbon recovery operations.

BRIEF DESCRIPTION OF THE DRAWINGS

Embodiments of the disclosure may be better understood by referencing the accompanying drawings.

DESCRIPTION OF EMBODIMENTS

Figure 1:
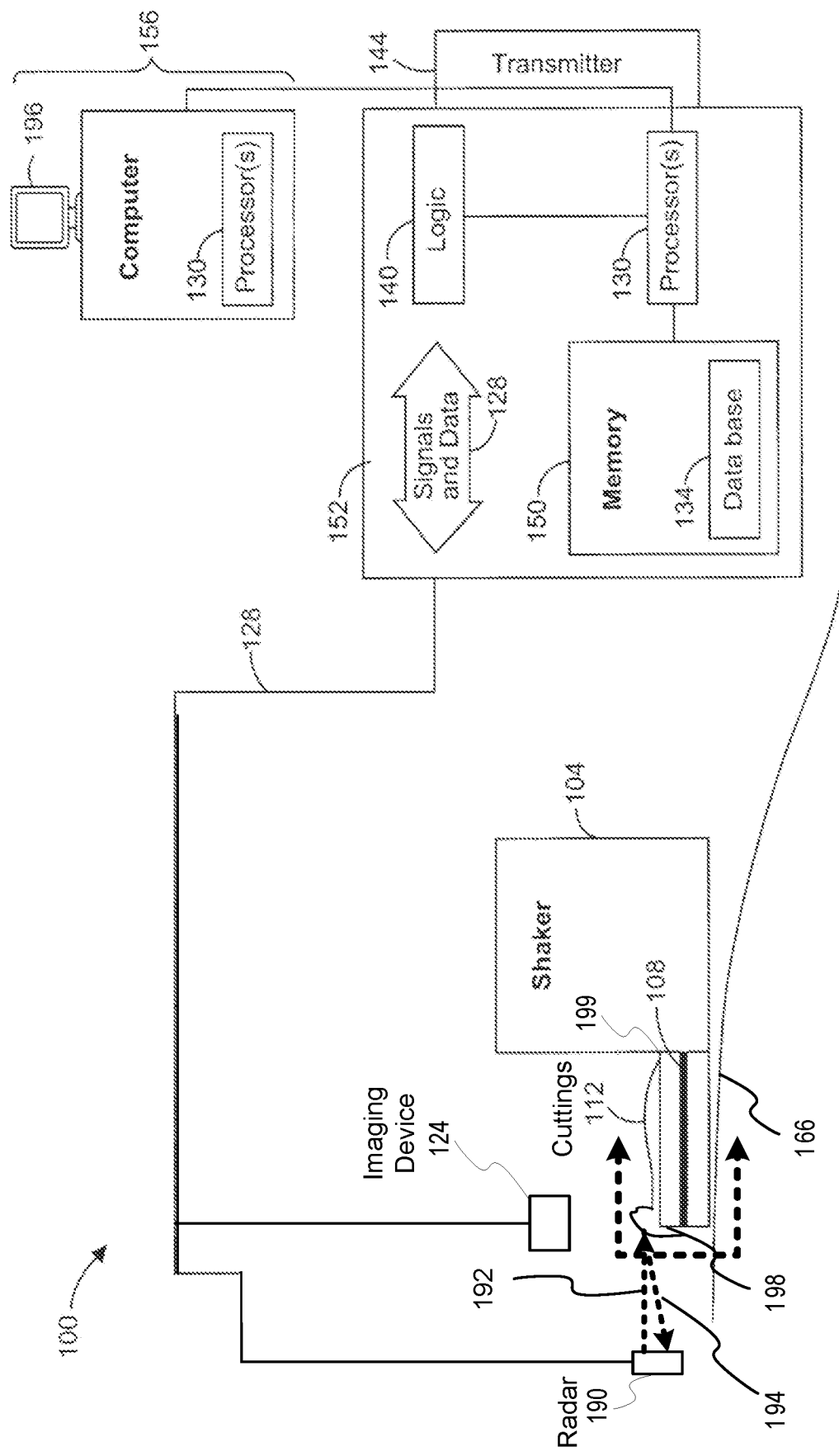
FIG. 1 is a block diagram of an example system for velocity-based volume measurement of downhole cuttings, according to some embodiments.

The description that follows includes example systems, methods, techniques, and program flows that embody aspects of the disclosure. However, it is understood that this disclosure may be practiced without these specific details. For instance, this disclosure refers to drilling as a downhole operation in illustrative examples. Aspects of this disclosure can also be applied to any other type of downhole operation that results in cuttings or any other downhole particles coming to the surface of the borehole (e.g., fracturing). In other instances, well-known instruction instances, protocols, structures and techniques have not been shown in detail in order not to obfuscate the description.

Various embodiments relate to measuring or determining a velocity of cuttings coming to the Earth's surface during a downhole operation (e.g., drilling) as the cuttings advance across a shaker. However, various embodiments should not be limited to measurement of velocity of drilled cuttings. Some embodiments can also be used for monitoring the shaker tilt angle, thereby monitoring health of the shaker as well as monitoring changes in the mud density or return mud rheological parameters that affect transport velocity. Both cuttings and fluids can come to the surface during the downhole operation. Accordingly, the cuttings and fluids are transferred to a top surface of the shaker. The top surface of the shaker can be a screen, such that fluids will fall through, leaving the cuttings. During operation, the shaker vibrates, and the screen can be configured as a conveyor to move the cuttings from a first end to a second end (or a "discharge end"), resulting in the cuttings falling off of the discharge end.

An approximate area of the cuttings on the shaker (known as "area under the curve") can also be measured or determined in addition to the velocity of cuttings. The velocity measurement and the approximate area of the cuttings on the shaker can be leveraged to determine a volume of the cuttings at or over a given time period. The total volume of the cuttings received from downhole and processed by the shaker for a given zone or location in the formation being drilled can then be determined by adding measurements of the volume of cuttings for the time periods that were associated with the cuttings from that given zone or location. The total volume of the cuttings can also be determined for a particular downhole operation, a given time of a particular downhole operation, etc.

Without measurement of the velocity of the cuttings, errors can occur when determining the volume of the cuttings. Conventional approaches for velocity measurement include approximation and inferences made from dropping a known particle on the shaker and measuring the time for the distance travelled. However, these conventional approaches are prone to inducing error in calculations. For example, these conventional approaches do not provide an ongoing read of velocity and do not account for changes in velocity. Also, such approaches can increase cost of the system substantially if this process of dropping a known particle at certain intervals of time is automated.

Various embodiments use radar (RAdio Detection And Ranging) to track the movement of the particles moving across a screen of the shaker. The selected radar can be a radar which transmits a narrow band of electromagnetic waves and can be high resolution. In some embodiments, the radar is positioned to emit electromagnetic waves at a discharge end of the shaker screen. This position of the radar ensures the velocities of the cuttings are being captured at the discharge end of the shaker screen rather than the middle of the shaker screen, where velocity of the cuttings can be higher.

The velocity obtained from the radar can be integrated into a cuttings volume platform that includes measuring an area of the cuttings moving across the shaker screen, or the area under the curve. A volume measurement of a cutting can be calculated by multiplying the velocity of a cutting by the area of the cuttings. Accordingly, a total volume measurement of the cuttings can be made by adding together a volume measurement of each cutting moving across the shaker screen. Using radar to measure velocity of a cutting moving along the shaker screen overcomes the challenges of vibration, variable ambient lighting, fog, mechanical variation, mud splash, high cost, etc. which introduce error in determining velocity with conventional approaches.

In some embodiments, an optical device can make optical measurements of the area of the cuttings. For example, optical devices can be positioned above a shaker screen to make optical measurements. Alternatively or in addition, optical devices can be positioned on the discharge end of the shaker screen to make optical measurements. Radar can also be used to determine shaker tilt. The velocity of the particles coming off the shaker can be correlated to the shaker tilt angle. Due to ongoing high frequency vibration, it is likely that changes in shaker tilt during the operation are undetected. However, knowledge of whether the shaker tilt angle has changed facilitates maintenance of shaker health. Excess downward tilt can cause higher velocity of the particles as well as loss of drilling mud and cuttings, thereby increasing the cost of operations. Conversely, excess upward tilt of the shaker may cause particles to stay on the shaker screen longer, slowing down velocity of the particles and eventually causing particles to settle in the shaker screen (or "blinding" of the shaker screen). Increase in return mud density or other rheological parameters can also cause the velocity of the particles to decrease. By utilizing the correlation between the velocity of the particles and shaker tilt, the health of the shaker and the shaker screen can be monitored as changes occur. Any substantial change in the velocity can be incorporated as an alarm, thereby providing more opportunities for health monitoring of the shaker or monitoring changes in the mud density or return mud rheological parameters that affect transport velocity.

Example System

FIG. 1 is a block diagram of an example system for velocity-based volume measurement of downhole cuttings, according to some embodiments. A system 100 comprises a combination of an imaging device 124, a radar 190, and one or more processors 130. The imaging device 124, the radar 190, and/or the processors 130 may be located above the surface 166 of a geological formation, perhaps forming part of a data acquisition system 152. In some embodiments, the imaging device 124 may comprise one or more CCD (charge coupled device) or CMOS (complimentary metal-oxide semiconductor) cameras, including low light or infrared cameras.

The system 100 may also include logic 140, perhaps comprising a programmable data acquisition subsystem. The logic 140 can be used to acquire live video stream information 128, and other data, such as information from downhole, including the depth of a drill bit during a drilling operation.

A memory 150, located above or below the surface 166, can be used to store acquired image data captured by the imaging device 124 and reflection data detected by the radar 190, as well as other data (e.g., perhaps in a database 134). The memory 150 is communicatively coupled to the processor(s) 130. The imaging device 124 and the radar 190 are communicatively coupled to the processors 130. The processors 130 can control the imaging device 124 and the radar 190. While depicting only one radar, the system 100 can include multiple radars that are positioned to emit an electromagnetic wave to a discharge end 198 of a shaker screen 108. Though FIG. 1 depicts the radar 190 as positioned towards a shaker screen, the system 100 may include any other transit placed downstream to the shaker 104 which is used to transport material, such as through vibration, plunger action, conveyor, or other means. The radar 190 can thus be positioned towards this transit.

During operation, cuttings 112 from downhole along with fluids are forwarded from the borehole and deposited onto the shaker screen 108 at its front end 199. The cuttings 112 and fluids move toward the discharge end 198 of the shaker screen, while a shaker 104 causes the shaker screen 108 to vibrate to more easily separate the cuttings 112 from the fluids. During this operation, the radar 190 emits an electromagnetic wave 192 toward the cuttings 112 at or near the discharge end 198. A reflection 194 of the electromagnetic wave is reflected off the cuttings and detected by the radar 190. As further described below, the reflections detected by the radar 190 are used to determine a velocity of the cuttings 112 as they move across the shaker screen 108. The angle of tilt of the shaker screen 108 may also be monitored during operation.

The imaging device 124 can capture images of the cuttings 112 on the shaker screen 108. As further described below, the images of the cuttings 112 can be used to determine an area of the cuttings 112. In turn, a volume of the cuttings 112 can be derived from the velocity and the area of the cuttings 112. The processors 130 may also be configured to publish the volume of cuttings 112 in conjunction with probable conditions associated with a borehole operation (e.g., drilling, fracturing, etc.). Alternatively or in addition, the processors 130 can modify the borehole operation based on the volume of cuttings 112.

The radar 190 can include the following: 1) a transmitter that creates the energy pulse; 2) a transmit/receive switch to control when an antenna of the radar 190 is to transmit pulses and when to receive pulses; 3) an antenna to transmit the pulses out into the atmosphere and to receive the reflected pulses; and 4) a receiver that detects, amplifies and transforms the received signals into video format. In some embodiments, the radar 190 operates in the microwave region of the electromagnetic spectrum at frequencies extending from approximately 400 MegaHertz (MHz) to 40 GigaHertz (GHz). The radar 190 can extract the frequency shift of the reflected signal produced by a moving target based on the difference between the frequency of the received signal and the frequency of the signal that was transmitted.

To capture velocity, a 4-20 milli-amp (mA) signal, RS-232/485, or any other communication protocol can be leveraged. The radar 190 can be connected to the data acquisition system 152 through armored or unarmored intrinsically safe cables. The data acquisition system 152 can use intrinsically safe barriers or may be a remote input/output (I/O) system. The data acquisition system 152 may be certified for Zone 1 classified hazardous locations. To minimize multiple cable runs, fiber/copper cable can run from a Zone 1 certified local data acquisition system 152 to a safe area (e.g., a mud logging device). The data acquisition system 152 can be connected to a network computer 156 and database, such as the database 134 in memory 150. Graphical user interfaces (GUIs) can be created to plot the velocity readings and/or trends on a display 196.

The velocity of the cuttings 112 can also be used to monitor its correlation with the shaker tilt angle, monitor the health of the shaker 104, and/or account for accidental and/or undesired changes to the shaker 104. Velocity can be monitored throughout the duration of operation to track sudden changes in the return mud density or other rheological properties that affect the transport velocity.

Figure 2:
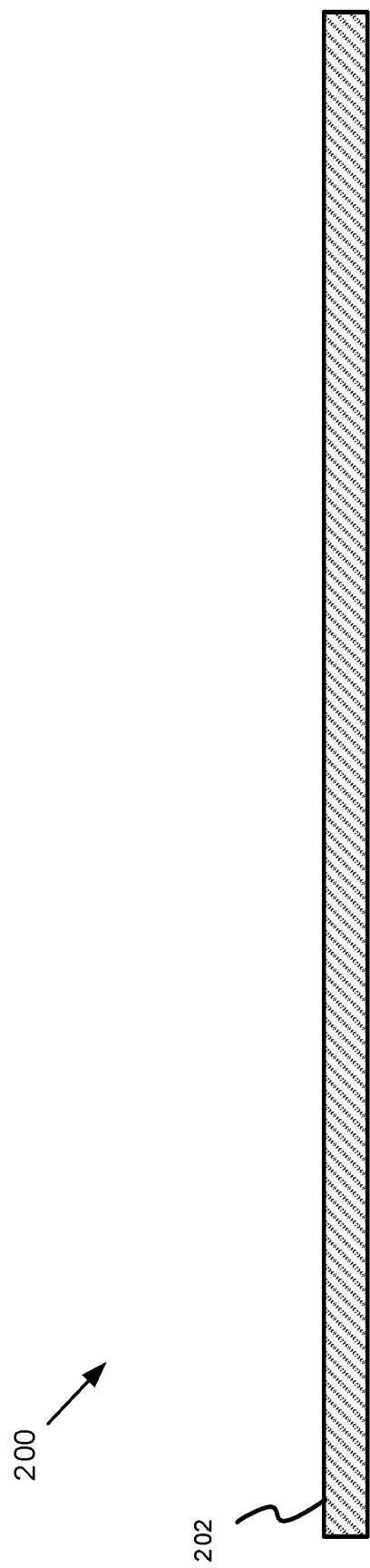
FIG. 2 is a side view of a discharge end of a shaker screen without cuttings, according to some embodiments.

FIG. 2 is a side view of a discharge end of a shaker screen without cuttings, according to some embodiments. In particular, FIG. 2 depicts a side view of a discharge end 202 of a shaker screen 200 that can be an example of the discharge end 198 of the shaker screen 108 depicted in FIG. 1. Cuttings (e.g., the cuttings 112) from downhole which are deposited onto the shaker screen 200 move across the shaker screen 200 towards the discharge end 202.

Figure 3:
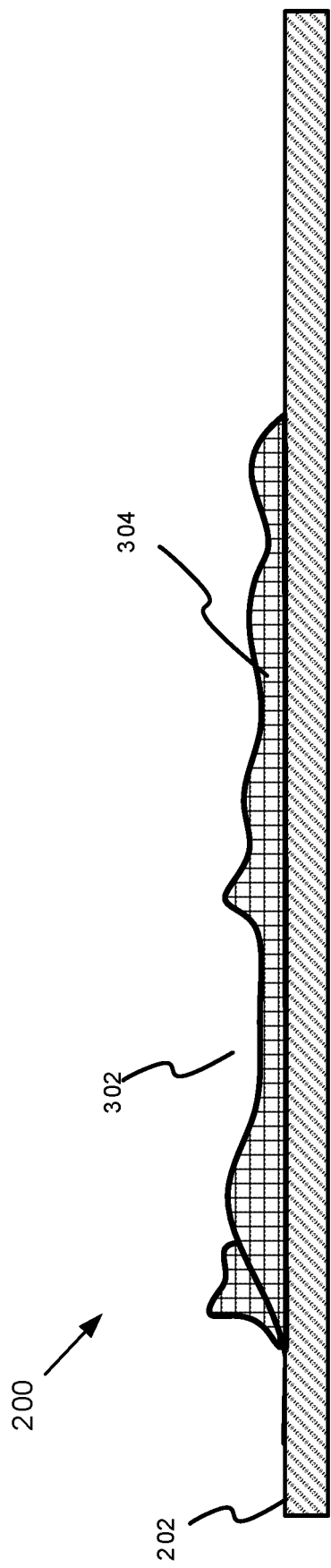
FIG. 3 is a side view of a discharge end of a shaker screen with cuttings, according to some embodiments.

FIG. 3 is a side view of a discharge end of a shaker screen with cuttings, according to some embodiments. In particular, FIG. 3 depicts a side view of the discharge end 202 of the shaker screen 200 of FIG. 2 that includes cuttings 302. An area 304 of the cuttings 302 can be determined by processing the images captured by the imaging device 124 (as further described below). While FIGS. 2-3 depict the shaker screen as a flat screen, the shaker screen can be any other type of screen (such as corrugated, etc.) A radar, such as the radar 190 of FIG. 1, captures velocity of the cuttings 302 as the cuttings 302 reach the discharge end 202 of the shaker screen 200. The radar 190 transmits an electromagnetic wave as to capture the velocity of the cuttings 302 as close as possible to the discharge end 202 to avoid contacting portions of the cuttings 302 which are closer to the center of the shaker screen 200. Volume measurements can be inaccurate if the velocity of the cuttings 302 is measured too far from the discharge end 202, as the velocity can be higher in this region of the shaker screen 200.

Example Operations

Figure 4:
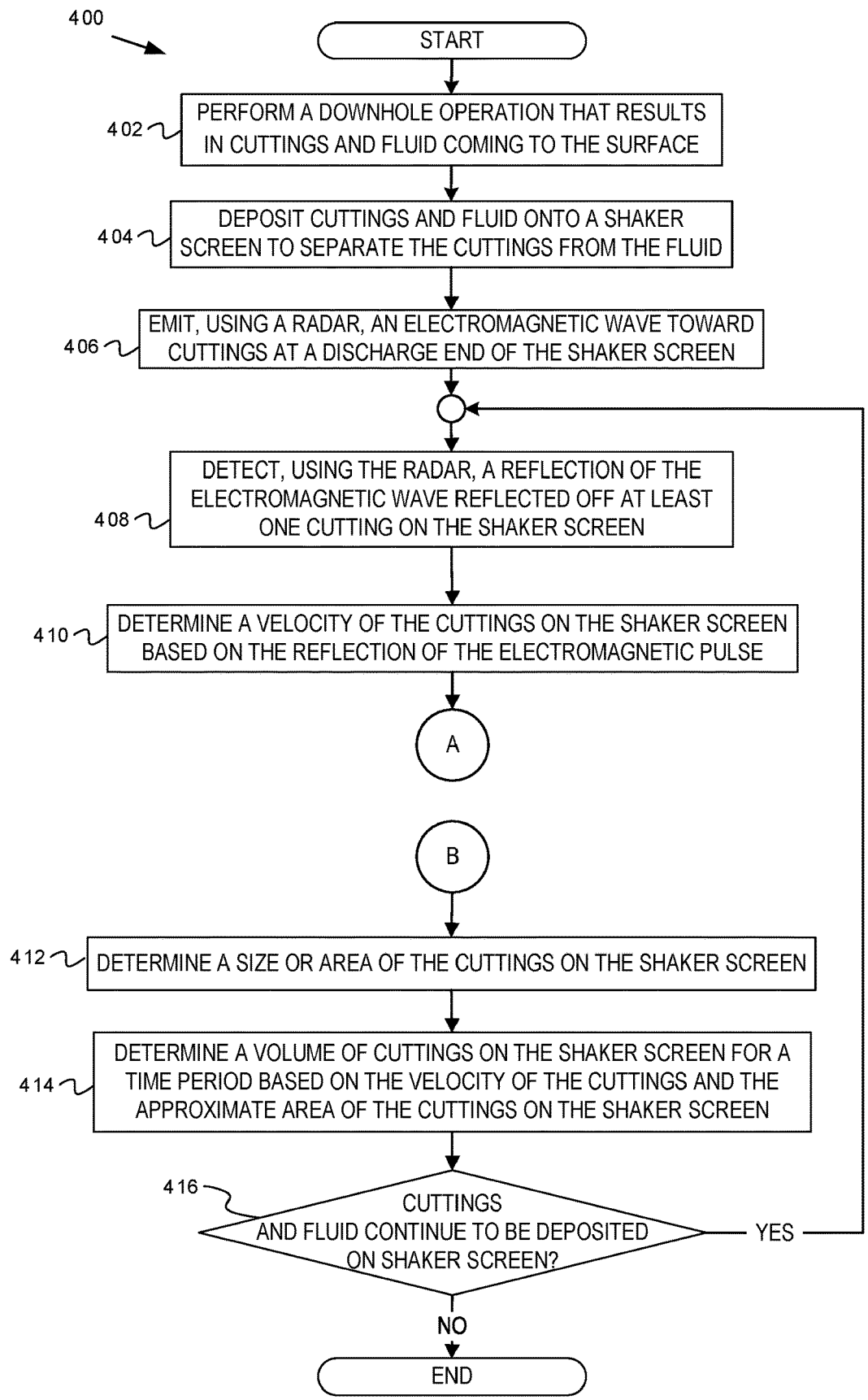
FIGS. 4-5 are flowcharts of operations for velocity-based volume measurement of downhole cuttings, according to some embodiments.
Figure 5:
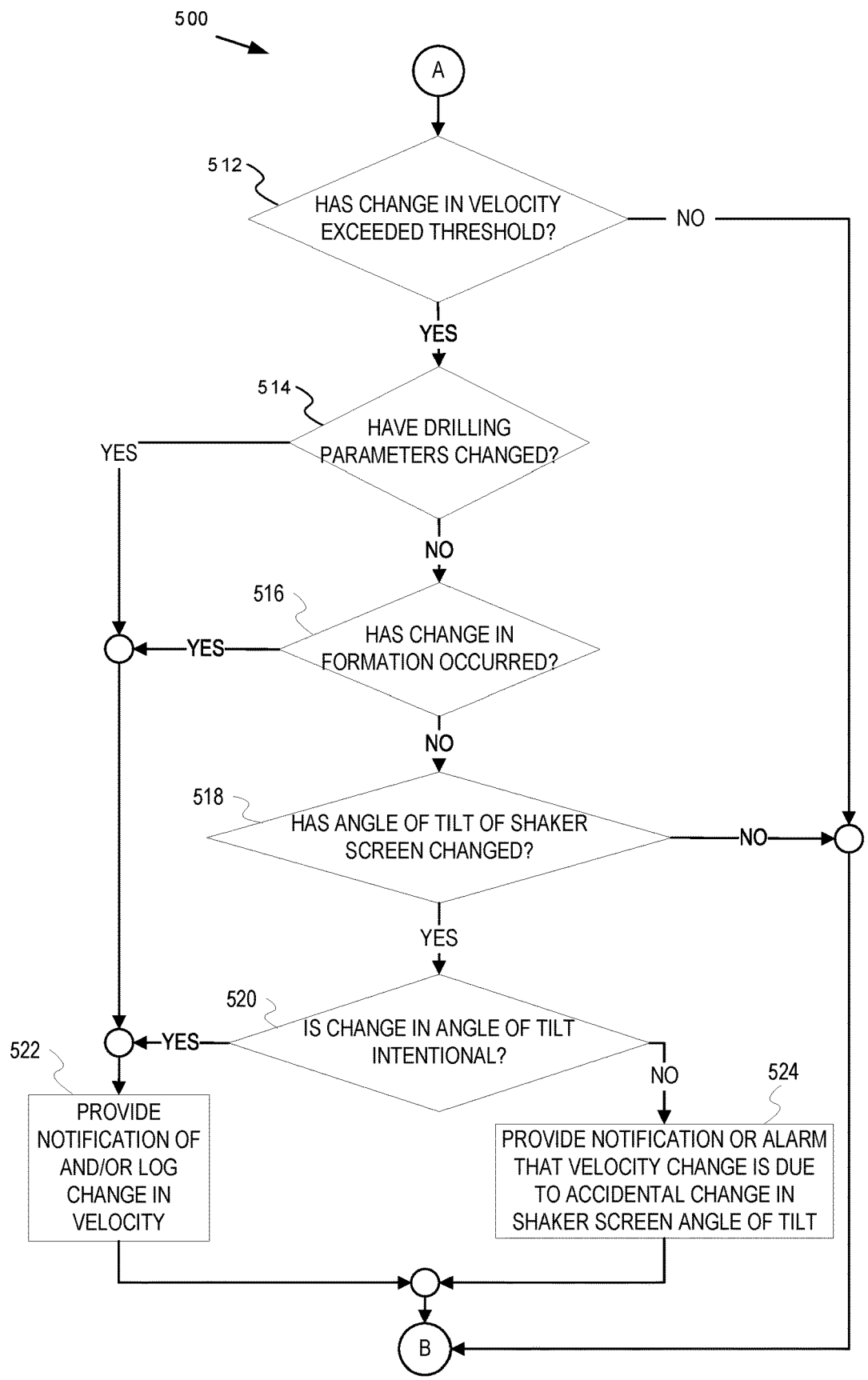

Example operations of determining volume cuttings based on velocity measurements and area of the cuttings are now described. FIGS. 4-5 are flowcharts of operations for velocity-based volume measurement of downhole cuttings, according to some embodiments. Operations of flowcharts 400-500 of FIGS. 4-5 continue among each other through transition points A-B. Operations of the flowcharts 400-500 can be performed by software, firmware, hardware, or a combination thereof. Operations of the flowchart 400 start at block 402.

At block 402, a downhole operation is performed that results in cuttings and fluid coming to the Earth's surface. For example, the downhole operation can be drilling, fracturing, etc. An example drilling operation is depicted in FIG. 5, which is further described below.

At block 404, the cuttings and fluid are deposited onto a shaker screen to separate the cuttings from the fluid. For example, referring to FIG. 1, fluid and the cuttings 112 are deposited onto the shaker screen 108.

At block 406, an electromagnetic wave is emitted, using a radar, toward the cuttings at a discharge end of the shaker screen. For instance, in FIG. 1, the radar 190 emits the electromagnetic wave 192 toward the cuttings 112 at the discharge end 198 of the shaker screen 108. As another example, the radar 190 emits the electromagnetic wave toward the cuttings 302 at the discharge end 202 of the shaker screen 200 depicted in FIG. 3.

At block 408, a reflection of the electromagnetic wave reflected off at least one cutting on the shaker screen is detected using the radar. As an example, in FIG. 1, the radar 190 detects the reflection 194 of the electromagnetic wave 192 which has reflected off at least one of the cuttings 112.

At block 410, a velocity of the cuttings on the shaker screen is determined based on the reflection of the electromagnetic pulse. For instance, referring to FIG. 1, the radar 190 processes the reflection 194 and determines a Doppler frequency based on the difference between the frequency of the electromagnetic wave 192 and the frequency of the reflection 194. The velocity can then be determined based on the Doppler frequency and the observed frequencies of the electromagnetic pulses. In some embodiments, the radar 190 can transmit the velocity of the cuttings 112 to the data acquisition system 152 for storage in the memory 150. Operations continue at transition point A, which continues at transition point A of the flowchart 500.

At block 512, a determination is made of whether a sudden change in the velocity of the cuttings has occurred. Changes in observed velocity may be indicative of the following changes: changes in the drilling parameters, downhole formation changes, or intentional or accidental changes to the upward or downward tilt of the shaker. A threshold change in velocity can be established which indicates a magnitude which is considered a change. The threshold value may indicate a maximum magnitude of the change in velocity which is permitted. For example, at least an X % increase or decrease in velocity over N measurements can be defined as sudden change in the velocity, wherein X and N can be set based on the type of formation, type or size of the shaker, depth of the borehole, etc. Examples of the value of X can be 5, 10, 50, etc. Examples of values of N can be 1, 2, 3, 10, etc. An increase in velocity can be indicative of potential excessive downward tilt of the shaker, while a decrease can be indicative of potential excessive upward tilt of the shaker. Changes in velocity may also be attributable to changes in the density of the drilling mud or other rheological properties of the drilling mud returning to the surface. Additionally, changes in drilling parameters and/or downhole formation changes may cause an increase in cuttings returning from downhole. A change in velocity may be a consequence of this increase in downhole returns. To facilitate monitoring of shaker or shaker screen health, if a sudden change in the velocity is observed, a notification which indicates the sudden change may be output. For example, with reference to FIG. 1, one or more velocity calculations stored in memory 150 may be analyzed by the processor(s) 130 to determine if a sudden change in velocity has occurred. If the change in velocity exceeds a threshold, operations continue at block 514. If the change in velocity does not exceed a threshold, operations continue at transition point B, which continues at transition point B of the flowchart 400.

At block 514, a determination is made of whether the drilling parameters have changed. The changes in the drilling parameters can be verified against a drilling log. For instance, with reference to FIG. 1, drilling parameters and logged changes to the drilling parameters can be stored in a drilling log in memory 150. The processor(s) 130 can retrieve logged drilling parameters from memory 150 to determine if a change has been made. If the drilling parameters have not changed, operations continue at block 516. If the drilling parameters have changed, operations continue at block 522.

At block 516, a determination is made of whether a change in the formation has occurred. Downhole formation changes can be verified by monitoring the depth of drilling operations and comparing the depth with geological formation graphs. For example, a depth of the drill bit can be compared to an expected formation condition depicted in a geological formation graph. If the geological formation condition corresponding to the drill bit depth has changed since a previous observation, it may be determined that the formation has changed. Comparison of volumes of drilling mud in the drilling well and drilling mud pit can be used alternatively or in addition for verification of downhole formation changes. For instance, with reference to FIG. 1, the processor(s) 130 may leverage drill bit depth data, volumes of drilling mud in the drilling well and drilling mud pit, and geological formation graphs stored in memory 150 for the analysis. If a change in the formation has not occurred, operations continue at block 518. If a change in the formation has occurred, operations continue at block 522.

At block 518, a determination is made of whether the angle of tilt of the shaker screen has changed. For instance, with reference to FIG. 1, a sensor can be mounted on the shaker screen 108 which captures the angle of tilt of the shaker screen 108. A threshold angle of tilt can be established which indicates a threshold measurement which constitutes a change. For example, the error threshold can be a maximum permitted magnitude of the change in angle of tilt of the shaker screen 108. As another example, the error threshold can establish a threshold increase or decrease in angle of tilt of X degrees over N measurements captured by the sensor of the shaker screen 108 (e.g., a threshold increase or decrease of 5 degrees captured over 3 measurements, etc.). The angle of tilt may have changed intentionally or accidentally (e.g., due to mechanical faults of the shaker 104). Detected changes in the angle of tilt of the shaker screen 108 may be logged in memory 150 for analysis (e.g., by the processor(s) 130) and/or indicated with a notification output to the display 196. If the angle of tilt of the shaker has changed, operations continue at block 520. If the angle of tilt of the shaker screen has not changed, operations continue at transition point B, which continues at transition point B of the flowchart 400.

At block 520, a determination is made of whether the change in angle of tilt of the shaker screen was intentional. Intentional changes to the angle of tilt of the shaker screen captured by the sensor may be logged. For instance, with reference to FIG. 1, the angle of tilt may be stored in memory 150 following an increase or decrease in angle of tilt of the shaker screen 108. The processor(s) 130 can verify that the detected angle of tilt of the shaker screen 108 has been logged to determine that the change was intentional. If the change in angle of tilt of the shaker screen was intentional, operations continue at block 522. If the change in the angle of tilt of the shaker screen was not intentional (i.e., was accidental), operations continue to block 524.

At block 522, a determination is made that the change in velocity is caused by a change in drilling parameters, a change in formation, and/or an intentional change in the angle of tilt of the shaker screen. A notification and/or alarm is generated which indicates that a change in velocity has been detected. The notification and/or alarm may indicate the underlying cause of the change in velocity. Alternatively or in addition, the velocity change event can be logged in an event log. For instance, with reference to FIG. 1, a notification and/or alarm can be generated and output to the display 196. The event may also be logged in memory 150. Operations continue at transition point B, which continues at transition point B of the flowchart 400.

At block 524, a determination is made that the change in velocity is caused by an accidental change in the angle of tilt of the shaker screen. Accidental changes in the angle of tilt of the shaker screen may arise due to mechanical wear, loosening of bolts in the shaker, etc., which can contribute to loss of drilling mud or may cause damage to the shaker screen. A notification or alarm may be output which indicates that the change in velocity of the cuttings is due to an accidental change in the angle of tilt of the shaker screen. Alternatively or in addition, the change in velocity and the change in angle of tilt due to unintentional causes may be logged (e.g., in an event log). For example, with reference to FIG. 1, the measured angle of tilt and the detected change in velocity may be recorded in an event log in memory 150. A notification or alarm can also be generated and output to the display 196. Operations continue at transition point B, which continues at transition point B of the flowchart 400.

At block 412, a size or area of the cuttings on the shaker screen is determined. In some embodiments, a size or area of the cuttings can be defined as an area of the cuttings ("area under the curve"). For instance, with reference to FIGS. 1 and 3, the imaging device 124 can capture an image of the cuttings 112 at the discharge end 198 of the shaker screen 108. The acquired image data is communicated to the data acquisition system 152. The area 304 of the cuttings 302 as captured in the image data can be determined based on analysis of the image data (e.g., by the processor(s) 130). As an example, the area 304 under the curve can be determined by identifying the "curve" formed by the upper boundary of the cuttings 302 at the discharge end 202 above the structure of the shaker screen 200. The area 304 which is then calculated is the area between the shaker screen 200 and the upper boundary, or the curve, of the cuttings 302 on the shaker screen 200. The area 304 of the cuttings 302 can be stored in memory 150.

At block 414, a volume of the cuttings on the shaker screen are determined based on the velocity of the cuttings and the area of the cuttings on the shaker screen. For example, in FIG. 1, the processor(s) 130 can calculate the volume of the cuttings 112 by retrieving from memory 150 the velocity and area of the cuttings 112. The processor(s) 130 calculate the volume of the cuttings 112 as the product of the velocity and the area. In some embodiments, the velocity may be determined less frequently than the approximate area of the cuttings because the velocity of the cuttings tends to change less frequently. For example, the velocity may be determined once every minute, every five minutes, every 10 minutes, etc., while an image of the cuttings is captured and processed every second, every five seconds, every 10 seconds, etc. Accordingly, the volume of cuttings may be calculated after each velocity determination and/or each area determination.

At block 416, a determination is made of whether cuttings and fluid continue to be deposited on the shaker screen. If so, operations of the flowchart 400 return to block 408. Otherwise, operations of the flowcharts 400-500 are complete.

Example Drilling Application

Figure 6:
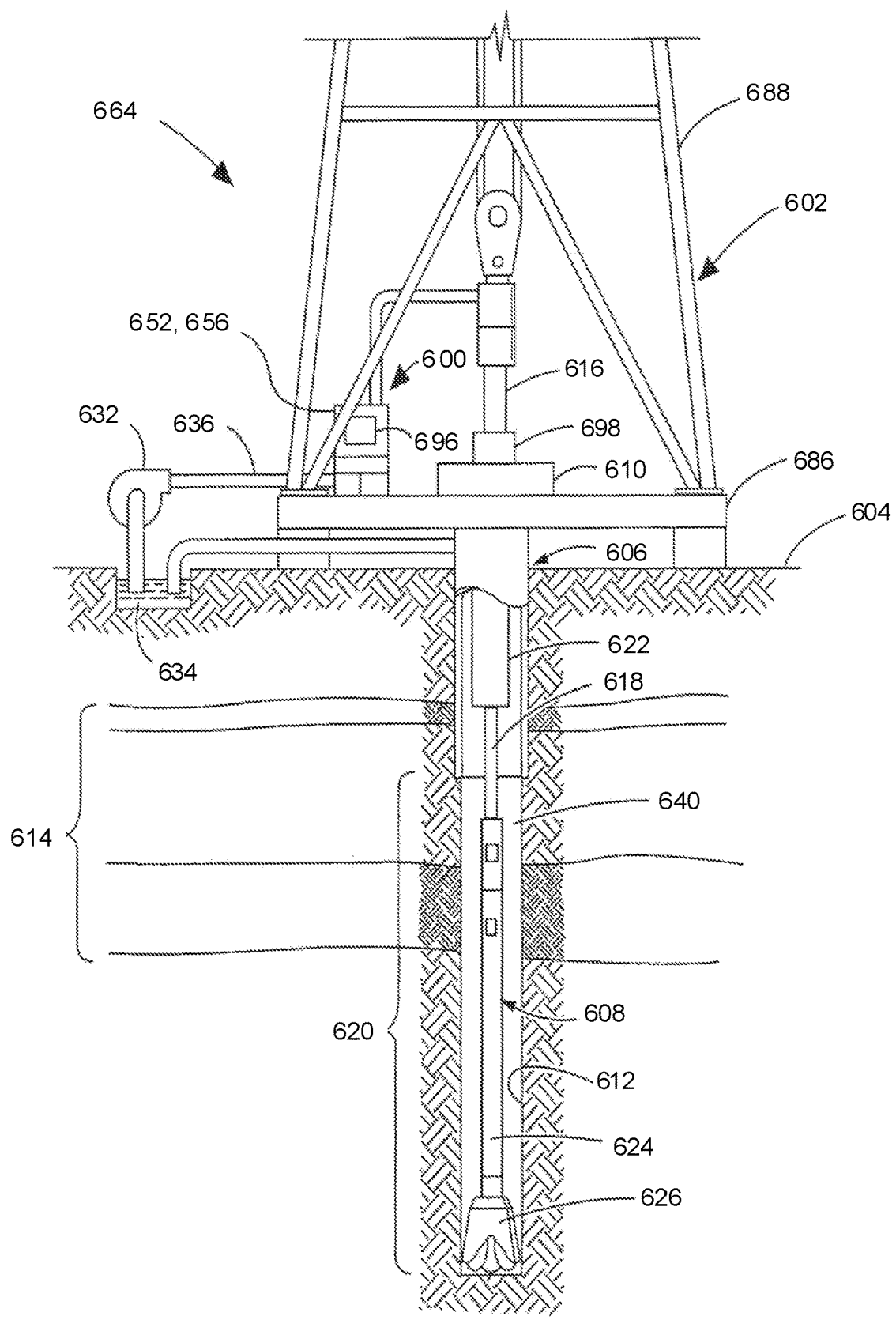
FIG. 6 is a schematic diagram of a drilling rig system, according to some embodiments.

FIG. 6 is a schematic diagram of a drilling rig system, according to some embodiments. For example, in FIG. 6 it can be seen how a system 664 may also form a portion of a drilling rig 602 located at the surface 604 of a well 606. Drilling of oil and gas wells is commonly carried out using a string of drill pipes connected together so as to form a drilling string 608 that is lowered through a rotary table 610 into a wellbore or borehole 612. Here, a drilling platform 686 is equipped with a derrick 688 that supports a hoist.

The drilling rig 602 may thus provide support for the drill string 608. The drill string 608 may operate to penetrate rotary table 610 for drilling the borehole 612 through subsurface formations 614. The drill string 608 may include a Kelly 616, drill pipe 618, and a bottom hole assembly 620, perhaps located at the lower portion of the drill pipe 618.

The bottom hole assembly 620 may include drill collars 622, a downhole tool 624, and a drill bit 626. The drill bit 626 may operate to create a borehole 612 by penetrating the surface 604 and subsurface formations 614. The downhole tool 624 may comprise any of a number of different types of tools including MWD tools, LWD tools, and others.

During drilling operations, the drill string 608 (perhaps including the Kelly 616, the drill pipe 618, and the bottom hole assembly 620) may be rotated by the rotary table 610. In addition to, or alternatively, the bottom hole assembly 620 may also be rotated by a motor (e.g., a mud motor) that is located downhole. The drill collars 622 may be used to add weight to the drill bit 626. The drill collars 622 may also operate to stiffen the bottom hole assembly 620, allowing the bottom hole assembly 620 to transfer the added weight to the drill bit 626, and in turn, to assist the drill bit 626 in penetrating the surface 604 and subsurface formations 614.

During drilling operations, a mud pump 632 may pump drilling fluid (sometimes known by those of ordinary skill in the art as "drilling mud") from a mud pit 634 through a hose 636 into the drill pipe 618 and down to the drill bit 626. The drilling fluid can flow out from the drill bit 626 and be returned to the surface 604 through an annular area 640 between the drill pipe 618 and the sides of the borehole 612. The drilling fluid may then be returned to the mud pit 634, where such fluid is filtered. In some embodiments, the drilling fluid can be used to cool the drill bit 626, as well as to provide lubrication for the drill bit 626 during drilling operations. Additionally, the drilling fluid may be used to remove subsurface formation 614 cuttings created by operating the drill bit 626. It is the images of these cuttings that many embodiments operate to acquire and process.

Thus, referring now to FIG. 1, it may be seen that in some embodiments, the system 664 may comprise a shaker screen 108 to receive drilling mud or fluid and cuttings, and the system 100 as described previously.

It should also be understood that the apparatus and systems of various embodiments can be used in applications other than for pumping and drilling operations, and thus, various embodiments are not to be so limited. The illustrations of the system 100 and the system 664 are intended to provide a general understanding of the structure of various embodiments, and they are not intended to serve as a complete description of all the elements and features of apparatus and systems that might make use of the structures described herein.

Applications that may include the novel apparatus and systems of various embodiments include electronic circuitry used in high-speed computers, communication and signal processing circuitry, modems, processor modules, embedded processors, data switches, and application-specific modules. Such apparatus and systems may further be included as sub-components within a variety of electronic systems, such as televisions, cellular telephones, personal computers, workstations, radios, video players, vehicles, signal processing for geothermal tools and smart transducer interface node telemetry systems, among others. Some embodiments include a number of methods.

Example Computer

Figure 7:
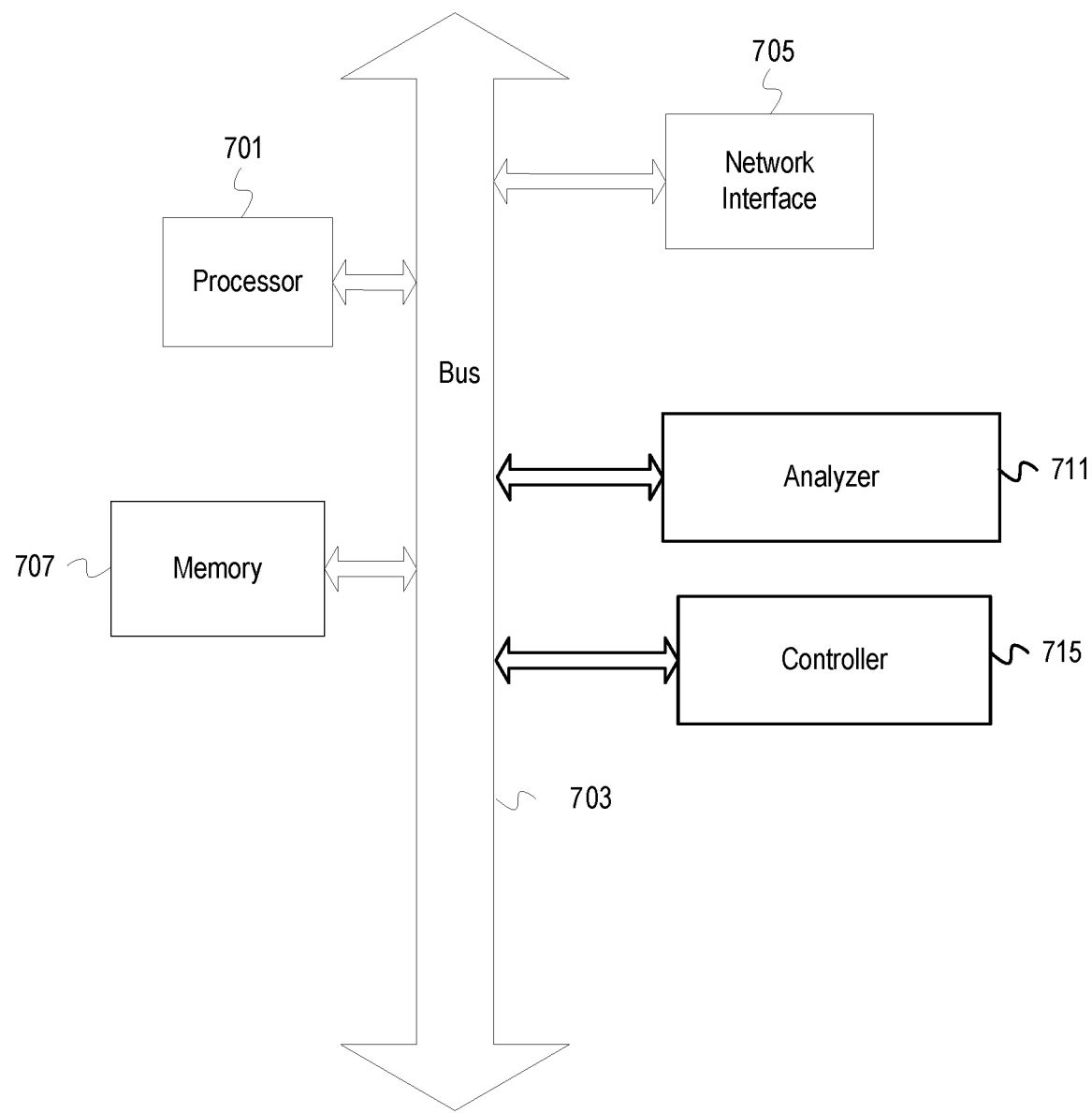
FIG. 7 is an example computer, according to some embodiments.

FIG. 7 depicts an example computer, according to some embodiments. The computer includes a processor 701 (possibly including multiple processors, multiple cores, multiple nodes, and/or implementing multi-threading, etc.). The computer includes memory 707. The memory 707 may be system memory (e.g., one or more of cache, SRAM, DRAM, zero capacitor RAM, Twin Transistor RAM, eDRAM, EDO RAM, DDR RAM, EEPROM, NRAM, RRAM, SONOS, PRAM, etc.) or any one or more of the above already described possible realizations of machine-readable media. The computer system also includes a bus 703 (e.g., PCI, ISA, PCI-Express, HyperTransport® bus, InfiniBand® bus, NuBus, etc.) and a network interface 705 (e.g., a Fiber Channel interface, an Ethernet interface, an internet small computer system interface, SONET interface, wireless interface, etc.).

The computer also includes an analyzer 711 and a controller 715. The analyzer 711 can perform processing and analyzing of the downhole cuttings based on the reflections of the electromagnetic waves and the captured images (as described above). The controller 715 can control the radar and imaging device as well as the different operations that can occur in the response to results from the analysis. For example, the controller 715 can communicate instructions to the appropriate equipment, devices, etc. to alter the drilling operations. Any one of the previously described functionalities may be partially (or entirely) implemented in hardware and/or on the processor 701. For example, the functionality may be implemented with an application specific integrated circuit, in logic implemented in the processor 701, in a co-processor on a peripheral device or card, etc. Further, realizations may include fewer or additional components not illustrated in FIG. 7 (e.g., video cards, audio cards, additional network interfaces, peripheral devices, etc.). The processor 701 and the network interface 705 are coupled to the bus 703. Although illustrated as being coupled to the bus 703, the memory 707 may be coupled to the processor 701. While depicted as a computer, some embodiments can be any type of device or apparatus to perform operations described herein.

It will be understood that each block of the flowchart illustrations and/or block diagrams, and combinations of blocks in the flowchart illustrations and/or block diagrams, can be implemented by program code. The program code may be provided to a processor of a general purpose computer, special purpose computer, or other programmable machine or apparatus.

As will be appreciated, aspects of the disclosure may be embodied as a system, method or program code/instructions stored in one or more machine-readable media. Accordingly, aspects may take the form of hardware, software (including firmware, resident software, micro-code, etc.), or a combination of software and hardware aspects that may all generally be referred to herein as a "circuit," "module" or "system." The functionality presented as individual modules/units in the example illustrations can be organized differently in accordance with any one of platform (operating system and/or hardware), application ecosystem, interfaces, programmer preferences, programming language, administrator preferences, etc.

Any combination of one or more machine readable medium(s) may be utilized. The machine-readable medium may be a machine-readable signal medium or a machine-readable storage medium. A machine-readable storage medium may be, for example, but not limited to, a system, apparatus, or device, that employs any one of or combination of electronic, magnetic, optical, electromagnetic, infrared, or semiconductor technology to store program code. More specific examples (a non-exhaustive list) of the machine-readable storage medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a machine-readable storage medium may be any tangible medium that can contain, or store a program for use by or in connection with an instruction execution system, apparatus, or device. A machine-readable storage medium is not a machine-readable signal medium.

A machine-readable signal medium may include a propagated data signal with machine readable program code embodied therein, for example, in baseband or as part of a carrier wave. Such a propagated signal may take any of a variety of forms, including, but not limited to, electromagnetic, optical, or any suitable combination thereof. A machine-readable signal medium may be any machine-readable medium that is not a machine-readable storage medium and that can communicate, propagate, or transport a program for use by or in connection with an instruction execution system, apparatus, or device.

Program code embodied on a machine-readable medium may be transmitted using any appropriate medium, including but not limited to wireless, wireline, optical fiber cable, RF, etc., or any suitable combination of the foregoing.

Computer program code for carrying out operations for aspects of the disclosure may be written in any combination of one or more programming languages, including an object oriented programming language such as the Java® programming language, C++ or the like; a dynamic programming language such as Python; a scripting language such as Perl programming language or PowerShell script language; and conventional procedural programming languages, such as the "C" programming language or similar programming languages. The program code may execute entirely on a stand-alone machine, may execute in a distributed manner across multiple machines, and may execute on one machine while providing results and or accepting input on another machine.

The program code/instructions may also be stored in a machine-readable medium that can direct a machine to function in a particular manner, such that the instructions stored in the machine-readable medium produce an article of manufacture including instructions which implement the function/act specified in the flowchart and/or block diagram block or blocks.

Using the apparatus, systems, and methods disclosed herein may provide the ability to monitor changes in downhole particles (e.g., cuttings), so that the impact of drilling fluid properties and activities in the field can be assessed immediately. This ability may be used to increase efficiency by redirecting pumping and drilling operations in real-time, perhaps as part of a closed-loop control system.

While the aspects of the disclosure are described with reference to various implementations and exploitations, it will be understood that these aspects are illustrative and that the scope of the claims is not limited to them. In general, techniques for processing and analyzing of particles from downhole as described herein may be implemented with facilities consistent with any hardware system or hardware systems. Many variations, modifications, additions, and improvements are possible.

Plural instances may be provided for components, operations or structures described herein as a single instance. Finally, boundaries between various components, operations and data stores are somewhat arbitrary, and particular operations are illustrated in the context of specific illustrative configurations. Other allocations of functionality are envisioned and may fall within the scope of the disclosure. In general, structures and functionality presented as separate components in the example configurations may be implemented as a combined structure or component. Similarly, structures and functionality presented as a single component may be implemented as separate components. These and other variations, modifications, additions, and improvements may fall within the scope of the disclosure.

Use of the phrase "at least one of" preceding a list with the conjunction "and" should not be treated as an exclusive list and should not be construed as a list of categories with one item from each category, unless specifically stated otherwise. A clause that recites "at least one of A, B, and C" can be infringed with only one of the listed items, multiple of the listed items, and one or more of the items in the list and another item not listed.

Example Embodiments

Example embodiments include the following:

Embodiment 1: A method comprising: depositing, onto a shaker screen, a plurality of downhole materials and fluids coming to a surface of a borehole as a result of a downhole operation in the borehole, wherein the downhole materials comprise cuttings; separating, using the shaker screen, the downhole materials from the fluids; emitting, using a radar, an electromagnetic wave toward at least one of a discharge end of the shaker screen and a transit; detecting a reflection of the electromagnetic wave reflected off at least a portion of the downhole materials; and determining, based on the reflection of the electromagnetic wave, a velocity of the downhole material advancing along at least one of the transit and the shaker screen toward the discharge end of the shaker screen.

Embodiment 2: The method of Embodiment 1, further comprising: determining an area of the at least the portion of the downhole materials; and determining a volume of the downhole materials based on the velocity of the downhole materials advancing along at least one of the shaker screen toward the discharge end of the shaker screen and the transit and the area of the at least the portion of the downhole materials.

Embodiment 3: The method of Embodiment 2, wherein determining the volume of the downhole materials comprises calculating a product of the velocity of the downhole materials and the area of the at least the portion of the downhole materials.

Embodiment 4: The method of any one of Embodiments 1-3, wherein determining the velocity of the downhole materials comprises: determining a difference in frequency between the electromagnetic wave emitted by the radar and the reflection of the electromagnetic wave; and calculating the velocity of the downhole materials, based on the difference in frequency.

Embodiment 5: The method of any one of Embodiments 1-4 further comprising correlating an angle of tilt of at least one of the shaker screen and the transit to the velocity of the downhole materials.

Embodiment 6: The method of Embodiment 5, further comprising determining that the angle of tilt of at least one of the shaker screen and the transit needs to be corrected based on correlating the angle of tilt of at least one of the shaker screen and the transit to the velocity of the downhole materials.

Embodiment 7: The method of Embodiment 6, wherein determining that the angle of tilt of at least one of the shaker screen and the transit needs to be corrected comprises: determining whether a change in the velocity of the downhole materials has exceeded a velocity threshold; and in response to the change in the velocity exceeding the velocity threshold, determining whether the change in the velocity is a result of a change in an angle of a tilt of at least one of the shaker screen and the transit exceeding an error threshold or an increase in an amount of downhole material returning from downhole; generating an alarm for a change in velocity; in response to the change in velocity being the result of the increase in the amount of downhole material returning from downhole, determining whether the increase in the amount of downhole material is a result of a change in drilling parameters or a change in formation being drilled and generating an alarm for increased velocity and determining a cause of increasing returns because of change in drilling parameters or a formation being drilled; and in response to the change in the velocity exceeding the velocity threshold being the result of the change in the angle of the tilt of at least one of the shaker screen and the transit exceeding the error threshold and that the change in the angle of the tilt was not intentional, generating an alarm that there is an error in the angle of the tilt of the at least one of the shaker screen and the transit.

Embodiment 8: One or more non-transitory machine-readable media comprising program code executable by a processor to cause a device to: receive a reflection value of a reflection of an electromagnetic wave that reflected off at least a portion of downhole materials deposited onto at least one of a shaker screen and a transit, wherein the reflection is based on emission of the electromagnetic wave from a radar toward at least one of a discharge end of the shaker screen and the transit; determine, based on the reflection value, a velocity of the downhole materials advancing along the shaker screen toward at least one of the discharge end of the shaker screen and the transit; determine an area of the downhole materials on at least one of the shaker screen and the transit; and determine a volume of the downhole materials based on the velocity of the downhole materials advancing along the shaker screen toward the discharge end of the shaker screen and the area of the downhole materials on the shaker screen.

Embodiment 9: The one or more non-transitory machine-readable media of Embodiment 8, wherein the program code to determine the volume of the downhole materials comprises program code executable by the processor to cause the device to calculate a product of the velocity of the downhole materials and the area of the downhole materials.

Embodiment 10: The one or more non-transitory machine-readable media of Embodiment 8 or 9, wherein the program code to determine the velocity of the downhole materials comprises program code executable by the processor to cause the device to: determine a difference in frequency between the electromagnetic wave emitted by the radar and the reflection of the electromagnetic wave; and calculate the velocity of the downhole materials, based on the difference in frequency.

Embodiment 11: The one or more non-transitory machine-readable media of any one of Embodiments 8-10 further comprising program code executable by the processor to cause the device to correlate an angle of tilt of at least one of the shaker screen and the transit to the velocity of the downhole materials.

Embodiment 12: The one or more non-transitory machine-readable media of Embodiment 11, further comprising program code executable by the processor to cause the device to determine that the angle of tilt of at least one of the shaker screen and the transit needs to be corrected based on correlation of the angle of tilt of at least one of the shaker screen and the transit to the velocity of the downhole materials.

Embodiment 13: The one or more non-transitory machine-readable media of Embodiment 12, wherein the program code to determine that the angle of tilt of at least one of the shaker screen and the transit needs to be corrected comprises program code executable by the processor to cause the device to: determine whether a change in the velocity of the downhole materials has exceeded a velocity threshold; in response to the change in the velocity exceeding the velocity threshold, determine whether the change in the velocity is a result of a change in an angle of a tilt of at least one of the shaker screen and the transit exceeding an error threshold or an increase in an amount of downhole material returning from downhole; generate an alarm for a change in velocity; in response to the change in velocity being the result of the increase in the amount of downhole material returning from downhole, determine whether the increase in the amount of downhole material is a result of a change in drilling parameters or a change in formation being drilled and generate an alarm for increased velocity and determining a cause of increasing returns because of change in drilling parameters or a formation being drilled; and in response to the change in the velocity exceeding the velocity threshold being the result of the change in the angle of the tilt of at least one of the shaker screen and the transit exceeding the error threshold and that the change in the angle of the tilt was not intentional, generate an alarm that there is an error in the angle of the tilt of the at least one of the shaker screen and the transit.

Embodiment 14: An apparatus comprising: a shaker screen onto which downhole materials and fluid from a borehole are to be placed, the downhole materials a product of a downhole operation; a shaker to vibrate the shaker screen to separate the downhole materials from the fluid; a radar to emit an electromagnetic wave onto the downhole materials on at least one of the shaker screen and a transit and detect a reflection of the electromagnetic wave reflected off at least a portion of the downhole materials; and a device to determine a velocity of the downhole materials advancing along at least one of the shaker screen toward a discharge end of the shaker screen and the transit.

Embodiment 15: The apparatus of Embodiment 14 further comprising the device to: determine an area of the downhole materials on at least one of the shaker screen and the transit; and determine a volume of the downhole materials based on the velocity of the downhole materials advancing along at least one of the shaker screen toward the discharge end of the shaker screen and the transit and the area of the downhole materials on at least one of the shaker screen and the transit.

Embodiment 16: The apparatus of Embodiment 15, wherein the device to determine the volume of the downhole materials comprises the device to calculate a product of the velocity of the downhole materials and the area of the downhole materials.

Embodiment 17: The apparatus of any one of Embodiments 14-16, wherein the device to determine the velocity of the downhole materials comprises the device to: determine a difference in frequency between the electromagnetic wave emitted by the radar and the reflection of the electromagnetic wave; and calculate the velocity of the downhole materials, based on the difference in frequency.

Embodiment 18: The apparatus of any one of Embodiments 14-17 further comprising the device to correlate an angle of tilt of at least one of the shaker screen and the transit to the velocity of the downhole materials.

Embodiment 19: The apparatus of Embodiment 18, further comprising the device to determine that the angle of tilt of at least one of the shaker screen and the transit needs to be corrected based on correlation of the angle of tilt of at least one of the shaker screen and the transit to the velocity of the downhole materials.

Embodiment 20: The apparatus of Embodiment 19, wherein the device to determine that the angle of tilt of at least one of the shaker screen and the transit needs to be corrected comprises the device to: determine whether a change in the velocity of the downhole materials has exceeded a velocity threshold; and in response to the change in the velocity exceeding the velocity threshold, determine whether the change in the velocity is a result of a change in an angle of a tilt of at least one of the shaker screen and the transit exceeding an error threshold or an increase in an amount of downhole material returning from downhole; generate an alarm for a change in velocity; in response to the change in velocity being the result of the increase in the amount of downhole material returning from downhole, determine whether the increase in the amount of downhole material is a result of a change in drilling parameters or a change in formation being drilled and generate an alarm for increased velocity and determining a cause of increasing returns because of change in drilling parameters or a formation being drilled; and in response to the change in the velocity being the result of the change in the angle of the tilt of at least one of the shaker screen and the transit exceeding the error threshold and that the change in the angle of the tilt was not intentional, generate an alarm that there is an error in the angle of the tilt of the at least one of the shaker screen and the transit.

What is claimed is:

1. An apparatus comprising:
a shaker screen onto which downhole materials and fluid from a borehole are to be placed, the downhole materials a product of a downhole operation;
a shaker to vibrate the shaker screen to separate the downhole materials from the fluid;
a radar to emit an electromagnetic wave onto the downhole materials on at least one of the shaker screen or a transit and to detect a reflection of the electromagnetic wave reflected off at least a portion of the downhole materials; and
a device to determine a velocity of the downhole materials advancing along at least one of the shaker screen toward a discharge end of the shaker screen or the transit, based on a Doppler frequency associated with the reflection, the device to determine that a tilt angle needs to be corrected based on correlation of the tilt angle to the velocity of the downhole materials, the device to generate an alarm when a change in the velocity is determined to exceed a velocity threshold, and the device to determine whether the change in the velocity is a result of a change in the tilt angle exceeding an error threshold or a result of an increase in an amount of the downhole materials returning from downhole.

2. The apparatus of claim 1 further comprising the device to:
determine an area of the downhole materials on at least one of the shaker screen and the transit; and
determine a volume of the downhole materials based on the velocity of the downhole materials advancing along at least one of the shaker screen toward the discharge end of the shaker screen and the transit and the area of the downhole materials on at least one of the shaker screen and the transit.

3. The apparatus of claim 2, wherein the device to determine the volume of the downhole materials comprises the device to calculate a product of the velocity of the downhole materials and the area of the downhole materials.

4. The apparatus of claim 1, wherein the device to determine the velocity of the downhole materials comprises the device to:
determine a difference in frequency between the electromagnetic wave emitted by the radar and the reflection of the electromagnetic wave; and
calculate the velocity of the downhole materials, based on the difference in frequency.

5. The apparatus of claim 1, further comprising the device to correlate an angle of tilt of at least one of the shaker screen and the transit to the velocity of the downhole materials.

6. The apparatus of claim 1, wherein the tilt angle comprises an angle of tilt of at least one of the shaker screen or the transit.

7. The apparatus of claim 1, wherein the device is to:
in response to the change in velocity being the result of the increase in the amount of downhole material returning from downhole,
determine whether the increase in the amount of downhole material is a result of a change in drilling parameters or a change in formation being drilled and generate an alarm for increased velocity and determining a cause of increasing returns because of the change in drilling parameters or the formation being drilled; and
in response to the change in the velocity being the result of the change in the tilt angle of the tilt exceeding the error threshold and that the change in the tilt angle was not intentional, generate an alarm that there is an error in the tilt angle.

* * * * *